(12) United States Patent
Cattelin

(10) Patent No.: US 6,576,670 B1
(45) Date of Patent: *Jun. 10, 2003

(54) USE OF A 5HT$_{2A}$ AND 5HT$_{2A/C}$ RECEPTOR ANTAGONIST FOR TREATING SNORING AND HIGH RESISTANCE SYNDROME OF UPPER ANATOMICAL AIRWAYS

(75) Inventor: Françoise Cattelin, Paris (FR)

(73) Assignee: Sanofi_Synthelabo, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/868,532

(22) PCT Filed: Dec. 14, 1999

(86) PCT No.: PCT/FR99/03122

§ 371 (c)(1),
(2), (4) Date: Jun. 19, 2001

(87) PCT Pub. No.: WO00/37068

PCT Pub. Date: Jun. 29, 2000

(30) Foreign Application Priority Data

Dec. 22, 1998 (FR) ............................................. 98/16295

(51) Int. Cl.$^7$ ............................................. A61K 31/18
(52) U.S. Cl. ....................................................... 514/640
(58) Field of Search ................................ 514/640, 317, 514/923, 633

(56) References Cited

U.S. PATENT DOCUMENTS

| | | | |
|---|---|---|---|
| 5,166,416 A | | 11/1992 | Congy et al. |
| 5,290,951 A | | 3/1994 | Congy et al. |
| 5,844,000 A | * | 12/1998 | Brian et al. .................. 514/663 |
| 6,143,792 A | * | 11/2000 | Cattelin ....................... 514/640 |
| 6,277,864 B1 | * | 8/2001 | Mondadori et al. ......... 514/317 |

FOREIGN PATENT DOCUMENTS

| | | |
|---|---|---|
| EP | 373998 | 6/1990 |
| WO | WO 91/18602 | 12/1991 |
| WO | WO 98/38189 | 9/1998 |
| WO | WO 99/00119 | 1/1999 |
| WO | WO 99/43319 | 9/1999 |

OTHER PUBLICATIONS

"Further evidence that various 5–HT receptor subtypes modulate central respiratory activity: in vivo studies with SR 46349B", Monteau et al, European Journal of Pharmacology 259 (1994) 71–74.*
Derwent Patent Abstract No. 199908 (2001).
Derwent Patent Abstract No. 199840 (2001).
Veasey et al., Am. J. Respir. and Crit. Care Med., vol. 153, No. 2, 1996, pp. 776–786.
Yoshioka et al., The J. of Pharmacology and Exper. Ther., vol. 260, No. 2, 1992, pp. 917–924.
Radulovacki, Sleep, vol. 21. No. 2 1998, pp. 131–136.
Biosis Online Abstract No. XP002135598 (1998).

* cited by examiner

Primary Examiner—Zohreh Fay
Assistant Examiner—Brian-Yong S. Kwon
(74) Attorney, Agent, or Firm—Michael D. Alexander; Paul E. Dupont

(57) ABSTRACT

The invention relates to the use of 5HT$_{2A}$ AND 5HT$_{2A/C}$ receptor antagonists for the treatment of snoring and upper airway high resistance syndrome.

6 Claims, No Drawings

USE OF A 5HT$_{2A}$ AND 5HT$_{2A/C}$ RECEPTOR ANTAGONIST FOR TREATING SNORING AND HIGH RESISTANCE SYNDROME OF UPPER ANATOMICAL AIRWAYS

This application is a 371 of PCT/FR99/03122 Dec. 14, 1999.

The present invention relates to a novel use of antagonists of various serotonin receptors, namely the antagonists of the 5HT$_{2A}$ and 5HT$_{2A\text{-}2C}$ receptors for serotonin, preferably antagonists which are specific for said receptors. Among these antagonists specific for the 5HT$_{2A}$ and 5HT$_{2A\text{-}2C}$ receptors, it is possible to distinguish several compounds or families of compounds.

1-(2-Fluorophenyl)-3-(4-hydroxyphenyl)prop-2-en-1-one-O-2-dimethylaminoethyl)oxime of formula (I) and its pharmaceutically acceptable salts are described in European Patent 0 373 998 B1 as 5HT$_2$ receptor antagonists:

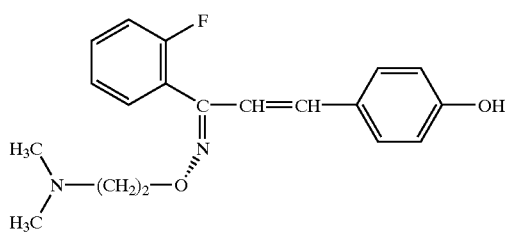

(I)

More particularly, (1Z,2E)-1-(2-fluorophenyl)-3-(4-hydroxyphenyl)prop-2-en-1-one-O-(2-dimethylaminoethyl) oxime hemifumarate, known under the code name SR 46349B and called hereinafter compound A, has been studied for its biochemical and pharmacological properties. Compound A is an antagonist which is specific for the 5HT$_{2A}$ receptor, that is to say it has no affinity for the 5HT$_{1A}$, 5HT$_{1B}$, and 5HT$_{1D}$ receptors, and has a moderate affinity for the 5HT$_{2C}$ receptor; in studies on isolated tissues, the absence of activity of compound A on rat stomach fundus indicates a 5HT$_{2A}$ specificity versus 5HT$_{2B}$ (M. Rinaldi-Carmona et al., J. Pharmacol. Exp. Ther., 1992, 262, 2, 759–768). In rodents, it has been shown that this compound predominantly binds to the regions of the brain containing the 5HT$_2$ receptor (M. Rinaldi-Carmona et al., Life Sciences, 1993, 54, 119–127).

(+)-(R)-α-(2,3-Dimethoxyphenyl)(1-[2-(4-fluorophenyl) ethyl]-4-piperidin-4-yl)methanol of formula (II) whose code name is MDL 100907 is known to be a 5HT$_{2A}$ receptor antagonist (J. Pharmacol. Exp. Therap., 1996, 277, 968–981).

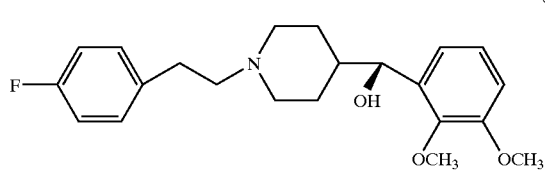

(II)

International Patent Application WO 98/38189 describes oxazolidine derivatives of formula (III) having 5HT$_{2A}$ receptor-antagonizing properties:

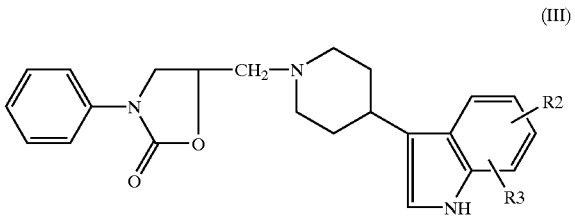

(III)

(S)-2-[[(7-Fluoro-2,3-dihydro-1H-inden-4-yl)-oxy] methyl]morpholine hydrochloride whose code name is YM 992 is a 5HT$_{2A}$ receptor antagonist described by Takeuchi H. et al. in Eur. J. Pharmacol. 1997, 329, 27–35.

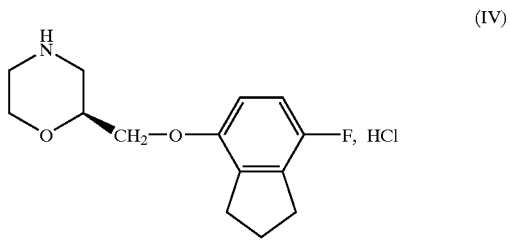

(IV)

Fananserin of formula:

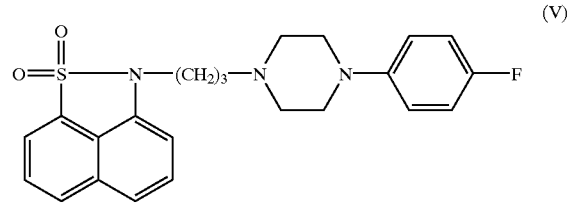

(V)

is also a 5HT$_{2A}$ receptor antagonist described by Doble A. et al., in Br. J. Pharmacol., 1992, 105, 27–36.

Studies on sleep have shown that some 5HT$_2$ receptor antagonists such as ritanserin, amoxapine and ICI 169 369 modify the architecture of sleep and regulate or increase slow wave sleep time (G. Loas, L'encéphale, 1991, XVII, 423–425).

The central mechanisms by which serotinin modulates the respiratory activity have been studied and it has been found that among the various families of receptors, only the 5HT$_1$ receptors and the 5HT$_2$ receptors affect the nerve control of the respiratory muscles (R. Monteau et al., Eur. J. Pharmacol., 1994, 259, 71–74).

In the same article, these authors studied in vitro on tissue preparations from newborn rats, with the aid of compound A, which sub-types of receptors are involved in the modulation of the respiratory activity. They observed that pretreatment with compound A prevents or significantly reduces the tonic cervical activity induced by 5-hydroxytryptamine and attributed to the activation of the spinal 5HT$_2$ receptors; likewise, it inhibits the depressant effect of 5-hydroxytryptamine on the activity of the hypoglossal nerve. Moreover, the authors suggest that compound A could be used for the in vivo study of the mechanisms responsible for obstructive apnea.

The use of L-tryptophan, a precursor of serotonin, in respiratory disorders of sleep has been studied in humans (H.

S. Schmidt, Bull. Eur. Physiopathol. Respir., 1983, 19, 625–629) as well as that of fluoxetine, a selective inhibitor of serotonin reuptake (Hanzel D. A., Chest, 1991, 100, 416–421).

European Patent Application EP 449 561 A indicates the use of (R)-fluoxetine for treating various conditions including sleep apneas.

An article by M. Yoshioka et al., in J. Pharmacol. Exp. Ther., 1992, 260 (2), 917–924 relates to the pharmacological characterization of apnea induced by 5-HT in rats; it reports that $5HT_2$ receptor antagonists such as ketanserin and methysergide inhibit apnea and the increase in pulmonary resistance induced by 5-HT, and shows that a $5HT_2$ agonist inhibits respiration in a manner identical to 5-HT. This article suggests that 5-HT-induced apnea is in part mediated by the vagal system.

S. C. Veasey et al., (Am. J. Respir. Crit. Care Med., 1996, 153, 776–786) have studied the effects of two serotonin antagonists on an animal model (the English bulldog) of respiratory disorders of sleep occurring during rapid-eye-movement sleep. They concluded that ritanserin and methysergide which antagonize in particular the $5HT_2$ receptors, when administered systemically, lead to a marked reduction in the activity of the dilatory muscle of the upper respiratory tracts and to a slight reduction in the activity of the diaphragm, these reductions coinciding with oxyhemoglobin desaturations. The authors suggest that serotonin could play a role in the increase in dilatory activity for the upper respiratory tracts during rapid-eye-movement sleep.

D. Rose et al., (Fundam. Clin. Pharmacol., 1996, 10 (1), 80) have reported the results of studies carried out in vivo on decerebrated newborn animals (rats and cats). In cats, they observed that the administration of high doses of 5-hydroxytryptamine induced prolonged central apneas linked to periods of active expiration. In rats, they observed no apnea after administration of 5-hydroxytryptamine, which is in contradiction with the results observed in vitro in newborn rats.

The interspecies differences observed on the respiratory mechanisms as well as the differences between the results of the studies in vivo and in vitro in rats give no indication to persons skilled in the art on the potential effect of the antagonists specific for the $5HT_{2A}$ or $5HT_{2A-2C}$ receptors on respiratory disorders linked to sleep in humans.

Unexpectedly, it has now been found that the $5HT_{2A}$ or $5HT_{2A-2C}$ receptor antagonists, in particular the compounds of formula (I), in particular compound A, and the compound of formula (II), are effective in the treatment of snoring and of upper airway high resistance or resistance syndrome.

Thus, the present invention relates to the use of a $5HT_{2A}$ or $5HT_{2A-2C}$ receptor antagonist, in particular a compound of formula (I) and the compound of formula (II), for the preparation of medicines useful in the treatment of snoring and of upper airway high resistance or resistance syndrome.

The present invention also relates to a pharmaceutical composition for the treatment of snoring and of upper airway high resistance or resistance syndrome comprising a $5HT_{2A}$ or $5HT_{2A-2C}$ receptor antagonist.

Furthermore, the invention relates to a method of treating snoring and upper airway high resistance or resistance syndrome comprising the administration of an effective quantity of a $5HT_{2A}$ or $5HT_{2A-2C}$ receptor antagonist.

Upper airway high resistance or resistance syndrome has been described by C. Guilleminault et al., in Chest, 1993, 104 (3), 781–787. It consists of repeated wakefulness visible on the electroencephalogram and accompanied by an increase in respiratory effort, indicated by a negative esophageal pressure.

The clinical consequences of upper airway resistance syndrome may include:
i) excessive somnolence during the day and secondarily loss of productivity, or even risks of accidents;
ii) chronic fatigue, irritability, nycturia, morning headaches, memory and/or personality disorders; an increase in susceptibility to cardiovascular complications such as pulmonary hypertension, cardiac insufficiency, systemic arterial hypertension, cardiac arrhythmias, stroke and myocardial infarction.

It has now been found that the $5HT_{2A}$ or $5HT_{2A-2C}$ receptor antagonists, preferably the antagonists specific for said receptors, in particular the compound of formula (I), in particular compound A and the compound of formula (II) are active in humans in the treatment of the abovementioned sleep disorders.

In young (18 to 35 years old) healthy subjects, it has been found that the administration of compound A induces a doubling of the duration of stages 3 and 4 of slow wave sleep from the dose of 1 mg; stages 1 and 2 of slow wave sleep being slightly reduced and paradoxical sleep not being modified.

The effect of compound A is determined during a clinical study carried out according to a double blind design versus placebo in which patients with upper airway high resistance syndrome characterized by the presence of respiratory efforts with repeated wakefulness or microwakefulness and clinical symptoms such as diurnal somnolence and/or hypertension and/or fatigue and/or morning headache and/or nycturia, and the like took part.

One gelatin capsule containing an active dose of compound A, for example 5 mg, is administered daily with the evening meal. A marked reduction is observed in respiratory efforts and the number of wakings or microwakings as well as a reduction in clinical symptoms.

The compound of formula (I) and its pharmaceutically acceptable salts are prepared according to the description given in European Patent 0 373 998 B1.

The compound of formula (II) is prepared according to the description given in European Patent 0 531 410 B.

The compounds of formula (III) is prepared as described in International Application WO 98/38189.

The compound of formula (IV) is prepared according to the procedure described in International Application WO 94/18182.

The compound of formula (V) is prepared according to the method described in European Application EP 350 403.

In the pharmaceutical compositions of the present invention for oral, sublingual, subcutaneous, intramuscular, intravenous, transdermal, local or rectal administration, the active ingredient alone or in combination with another active ingredient may be administered in a unit form for administration, mixed with conventional pharmaceutical carriers, to animals and to human beings. The appropriate unit forms for administration comprise the forms for administration by the oral route such as tablets, gelatin capsules, powders, granules and oral solutions or suspensions, the forms for sublingual and buccal administration, aerosols, implants, the forms for subcutaneous, transdermal, intramuscular, intravenous and intranasal administration and the forms for rectal administration.

The daily dosage for the compound according to the invention is from 0.001 to 1 mg/kg, advantageously from 0.002 to 0.5 mg/kg, preferably from 0.005 to 0.2 mg/kg, to be administered as a single dose or in divided doses. The compounds are generally formulated as a dosage unit containing from 0.05 to 50 mg, advantageously from 0.1 to 25 mg, preferably from 0.2 to 10 mg, of active ingredient per dosage unit, to be administered once, twice or several times at the same time, as required. Although these dosages are examples of average situations there may be certain cases where higher or lower dosages are appropriate, and such dosages also belong to the invention. According to the usual practice, the dosage appropriate for each patient is determined by the doctor according to the mode of administration, the age, weight and response of said patient.

When a solid composition is prepared in tablet form, it is possible to add to the active ingredient, micronized or otherwise, a wetting agent and the whole is mixed with a pharmaceutical vehicle such as silica, starch, lactose, magnesium stearate, talc and the like. It is possible to coat the tablets with sucrose, various polymers or other appropriate materials or to treat them such that they have a prolonged or delayed activity and that they continuously release a predetermined quantity of active ingredient.

A preparation is obtained as gelatin capsules by mixing the active ingredient or the active ingredients with a diluent and incorporating the mixture obtained into soft or hard gelatin capsules.

A preparation in syrup or elixir form may contain the active ingredient or the active ingredients together with a sweetener, which is preferably calorie-free, methylparaben and propylparaben as antiseptics, as well as a taste-enhancing agent and an appropriate coloring.

The water-dispersible powders or granules may contain the active ingredient mixed with dispersing agents or wetting agents, or suspending agents, such as polyvinylpyrrolidone or polyvidone, as well as with sweeteners or flavor correctors.

For rectal administration, use is made of suppositories which are prepared with binders melting at the rectal temperature, for example cocoa butter or polyethylene glycols.

For parenteral administration, use is made of aqueous suspensions, isotonic saline solutions or sterile and injectable solutions which contain dispersing agents and/or solubilizing agents which are pharmacologically acceptable, for example propylene glycol or butylene glycol.

Thus, to prepare an aqueous solution for injection by the intravenous route, it is possible to use a cosolvent: an alcohol such as ethanol, a glycol such as polyethylene glycol or propylene glycol and a hydrophilic surfactant such as polysorbate 80. To prepare an oily solution for injection by the intra-muscular route, it is possible to solubilize the active ingredient with a triglyceride or a glycerol ester.

For transdermal administration, it is possible to use patches in multilaminated form or with a reservoir in which the active ingredient is in alcoholic solution.

The active ingredient may also be formulated in the form of microcapsules or microspheres, optionally with one or more carriers or additives.

The active ingredient may also be provided in the form of a complex with a cyclodextrin, for example an α-, β- or γ-cyclodextrin, 2-hydroxypropyl-β-cyclodextrin or methyl-β-cyclodextrin.

Among the prolonged release forms which are useful in the case of chronic treatments, implants may be used. These may be prepared in the form of an oily suspension or in the form of a suspension of microspheres in an isotonic medium.

According to the present invention, the oral forms for administration are preferred.

EXAMPLE 1

Gelatin Capsule Containing 0.1 mg of (1Z,2E)-1-(2-fluorophenyl)-3-(4-hydroxyphenyl)prop-2-en-1-one-O-(2-dimethylaminoethyl)oxime

| | |
|---|---|
| Compound A | 0.236 mg |
| Crystallized extrafine lactose monohydrate | 99.014 mg |
| Modified corn starch | 25 mg |
| Anhydrous colloidal silica | 0.11 mg |
| Magnesium stearate | 0.64 mg |
| For a finished opaque white gelatin capsule of size 0, containing | 125 mg |

EXAMPLE 2

Gelatin Capsule Containing 1 mg of (1Z,2E)-1-(2-fluorophenyl)-3-(4-hydroxyphenyl)prop-2-en-1-one-O-(2-dimethylaminoethyl)oxime

| | |
|---|---|
| Compound A | 1.18 mg |
| Crystallized extrafine lactose monohydrate | 451.42 mg |
| Modified corn starch | 114 mg |
| Anhydrous colloidal silica | 0.5 mg |
| Magnesium stearate | 2.9 mg |
| For a finished opaque white gelatin capsule of size 0, containing | 570 mg |

EXAMPLE 3

Gelatin Capsule Containing 5 mg of (1Z,2E)-1-(2-fluorophenyl)-3-(4-hydroxyphenyl)prop-2-en-1-one-O-(2-dimethylaminoethyl)oxime

| | |
|---|---|
| Compound A | 5.9 mg |
| Crystallized extrafine lactose monohydrate | 446.7 mg |
| Modified corn starch | 114 mg |
| Anhydrous colloidal silica | 0.5 mg |
| Magnesium stearate | 2.9 mg |
| For a finished opaque white gelatin capsule of size 0, containing | 570 mg |

EXAMPLE 4

Gelatin Capsule Containing 10 mg of (1Z,2E)-1-(2-fluorophenyl)-3-(4-hydroxyphenyl)prop-2-en-1-one-O-(2-dimethylaminoethyl)oxime

| | |
|---|---|
| Compound A | 11.8 mg |
| Crystallized extrafine lactose monohydrate | 440.8 mg |
| Modified corn starch | 114 mg |
| Anhydrous colloidal silica | 0.5 mg |
| Magnesium stearate | 2.9 mg |
| For a finished opaque white gelatin capsule of size 0, containing | 570 mg |

EXAMPLE 5

Gelatin Capsule Containing 20 mg of Formula (+)-(R)-α-(2,3-dimethoxyphenyl)(1-[2-(4-fluorophenyl)ethyl]-4-piperidin-4-yl)methanol

| | |
|---|---|
| (+)-(R)-α-(2,3-dimethoxyphenyl)(1-[2-(4-fluorophenyl)ethyl]-4-piperidin-4-yl)-methanol | 20 mg |
| Crystallized extrafine lactose monohydrate | 432.6 mg |
| Modified corn starch | 114 mg |
| Anhydrous colloidal silica | 0.5 mg |
| Magnesium stearate | 2.9 mg |
| For a finished opaque white gelatin capsule of size 0, containing | 570 mg |

What is claimed is:

1. A method for the treatment of snoring and upper airway high resistance or resistance syndrome which comprises administering to a patient in need of such treatment an effective amount of 1-(2-fluorophenyl)-3-(4-hydroxyphenyl)prop-2-en-1-one-O-2-(dimethylaminoethyl)-oxime or of one of its pharmaceutically acceptable salts.

2. A method according to claim 1 wherein the antagonist is (1Z,2E)-1-(2-fluorophenyl)-3-(4-hydroxyphenyl)prop-2-en-1-one-O-(2-dimethylaminoethyl)oxime hemifumarate.

3. A method according to claim 1 for treating snoring.

4. A method according to claim 1 for treating upper airway high resistance or resistance syndrome.

5. A method according to claim 2 for treating snoring.

6. A method according to claim 2 for treating upper airway high resistance or resistance syndrome.

* * * * *